United States Patent [19]

Neville et al.

[11] Patent Number: 5,725,857
[45] Date of Patent: *Mar. 10, 1998

[54] IMMUNOTOXIN WITH IN VIVO T CELL SUPPRESSANT ACTIVITY AND METHODS OF USE

[75] Inventors: David M. Neville, Bethesda; Joshua E. Scharff, Rockville, both of Md.

[73] Assignee: The United States of America as represented by the Department of Health and Human Services, Washington, D.C.

[*] Notice: The term of this patent shall not extend beyond the expiration date of Pat. No. 5,167,956.

[21] Appl. No.: 308,730

[22] Filed: Sep. 19, 1994

Related U.S. Application Data

[63] Continuation-in-part of Ser. No. 34,509, Mar. 19, 1993, abandoned, which is a continuation-in-part of Ser. No. 907,409, Jul. 1, 1992, abandoned, which is a continuation of Ser. No. 653,164, Feb. 11, 1991, Pat. No. 5,167,956.

[51] Int. Cl.$^6$ .................. A61K 39/395; C07K 16/28
[52] U.S. Cl. .................. 424/183.1; 424/178.1; 424/236.1; 424/238.1; 530/388.22; 530/388.7; 530/388.75; 530/391.7
[58] Field of Search .................. 424/183.1, 236.1, 424/238.1; 530/388.22, 388.7, 388.75, 391.7, 391.9

[56] References Cited

U.S. PATENT DOCUMENTS 5,167,956 12/1992 Neville et al. .................. 424/85.91

FOREIGN PATENT DOCUMENTS 0 306 943 8/1988 European Pat. Off. .

OTHER PUBLICATIONS

Oksenberg et al. *Nature* 362:68–70, Mar. 1993.
Laurence et al. *Nature* 358:255–259, Jul. 16, 1992.
Coffin, J.D. *Science* 255:411–413, Jan. 1992.
Vitetta et al. *Cancer Res.* 51:4052–4058, Aug. 1991.
Pastan et al. *Science* 254:1173–1177, Nov. 22, 1991.
zur Hausen *Science* 254:1167–1172, Nov. 1991.
Salmeron et al. *J. of Immunol.* 147(9):3047–3052, 1991.
Janeway, C. *Nature* 349(7):459–461, Feb. 1991.
Rostaing–Capaillon and Casellas *Cancer Research* 50:2909–2916, May 15, 1990.
Parlevliet et al. *Transplantation* 50:889–892, Nov. 1990.
Hirsch et al. *Transplantation* 49(6):1117–1123, Jun. 1990.
Izquierdo et al. *Int. J. Cancer* 43:697–702, 1989.
Kappler et al. *Science* 244:811–813, May 1989.
Neville et al. *J. Biol. Chem.* 264:14653–14661, 1989.
Gould et al. *J. Natl. Cancer Inst.* 81(10):775–781, May 22, 1989.
Myers et al. *J. Immunol. Methods* 121:129–142, 1989.
Urban et al. *Cell* 54:577–592, Aug. 12, 1988.
Hertler et al. *J. Biol. Resp. Modifiers* 7:97–113, 1988.
Johnson et al. *J. Biol. Chem.* 263(3):1295–1300, Jan. 1988.
Schaffar et al. *Cellular Immunol.* 116:52–59, 1988.
Nooij and Jonker *Eur. J. Immunol.* 17:1089–10093, 1987.
Greenfield et al. *Science* pp. 536–538, Oct. 23, 1987.
Nooij et al. *Eur. J. Immunol.* 16:975–979, 1986.
Thorpe et al. *NCI* (75(1):151–159, Jul. 1985.

Primary Examiner—Thomas M. Cunningham
Attorney, Agent, or Firm—Needle & Rosenberg, PC

[57] ABSTRACT

In one embodiment, the invention provides a method of treating an autoimmune disease in an animal comprising administering to the animal an antibody-CRM9 conjugate which routes by the anti-CD3 pathway, or derivatives thereof, under conditions such that the autoimmune disease is treated. In another embodiment, the invention provides an anti-Vβ-CRM9 immunoconjugate. In a further embodiment, the invention provides a method of treating T cell leukemias or lymphomas in an animal comprising administering to the animal an antibody-CRM9 conjugate which routes by the anti-CD3 pathway, or derivatives thereof, under conditions such that the T cell leukemias or lymphomas are treated.

6 Claims, 1 Drawing Sheet

IMMUNOTOXIN WITH IN VIVO T CELL SUPPRESSANT ACTIVITY AND METHODS OF USE

This application is a continuation-in-part of U.S. Ser. No. 08/034,509, filed Mar. 19, 1993 (now abandoned), which is a continuation-in-part of U.S. Ser. No. 07/907,409, filed Jul. 1, 1992 (now abandoned), which is a continuation of U.S. Ser. No. 07/653,164, filed Feb. 11, 1991, now U.S. Pat. No. 5,167,956, issued Dec. 1, 1992.

BACKGROUND OF THE INVENTION

1. Field of the Invention

The present invention relates to an immunotoxin. The invention further relates to a method of treating T cell leukemias or lymphomas, graft-versus-host diseases, and autoimmune diseases by administering an immunotoxin.

2. Background Information

Immunotoxins are toxins with altered receptor specificities. The alteration is achieved by coupling a monoclonal antibody (mAb) or growth factor to the toxin or toxin fragment. Plant and bacterial protein toxins intoxicate cells by a multi-step process whereby different toxin domains sequentially interact with cellular components. The intoxication pathway at a minimum consists of surface receptor binding, toxin processing, intracellular routing of toxin A chains to the cytosol, and enzymatic inactivation of protein synthesis (Neville and Hudson (1986) *Ann. Rev. Biochem.* 55:195). The goal of immunotoxin research has been to achieve targeted cell killing comparable to the enormous but indiscriminate cell killing power of the native toxins. An equally important goal has been to maintain the low non-target cell toxicity of toxin A chains, which lack cell receptor binding and membrane translocation functions (Youle and Neville (1982) *J. Clin. Biol.* 257:1598; Neville (1986)in CRC Crit. Rev., Therap. Drug Carrier Syst., CRC Press Inc., 2:329; Immunotoxins, Frankel ed.(1988) Kluwer Academic Publishers). Because of this latter consideration most in vivo clinical studies have focused on A chain immunotoxins or immunotoxins with truncated B chains lacking the receptor binding domain. While some clinical results have been encouraging, the reproducible achievement of both goals is at present uncertain (Program and Abstracts 2nd Int. Symposium on Immunotoxins, June 1990, Lake Buena Vista, Fla.).

Recently, Youle and co-workers have introduced highly efficacious holo-immunotoxins based on diphtheria toxin (DT) binding mutants (Greenfield et al. (1987) *Science* 238:536; Johnson et al. (1988) *J. Biol. Chem.* 263:1295; Johnson et al. (1989) *J. Neurosurg.* 70:240). These DT binding site mutants were equal to the wild-type immunotoxins in potency when directed at the human transferrin receptor (TFR) or human CD3, a component of the T cell receptor complex. Since the binding of the mutants was only 1/100–1/1000 of native DT, the toxin receptor appeared to be not needed along the intoxication pathway. This conclusion is limited to immunotoxins which route through CD3 and TFR, because similar immunotoxins directed at CD5 and the high-molecular weight-melanoma-associated antigen are relatively non-toxic (Neville et al. (1989) *J. Biol. Chem.* 264:14653). On the basis of data obtained with acid-cleavable conjugates which released free DT or the DT binding site mutant CRM9 in acidified endosomes, it was concluded that the DT receptor participates in the optimal intracellular routing of DT and many DT conjugates (Neville et al. (1989) *J. Biol. Chem.* 264:14653). It was also concluded that CD3 and TFR can perform the same routing function as the DT receptor, thus obviating the requirement of a DT receptor interaction for the binding site mutant conjugates anti-CD3-CRM9 and TFR-CRM9 (Intracellular routing of ricin based immunotoxins via the ricin receptor leading to enhanced efficacy has also been reported. Youle et al. (1981) *Cell* 23:551; Marsh and Neville (1986) *Biochem.* 25:4461; Youle and Colombatti (1987) *J. Biol. Chem.* 262:4676). Since anti-CD3-CRM9 appears to achieve optimal routing with low non-target cell toxicity as judged by in vitro assays, the present invention relates to a method of eradicating human CD3 bearing tumors in vivo.

The present invention provides in one embodiment, the immunotoxin anti-CD3-CRM9. The invention provides, in further embodiments, methods of treating T cell leukemias or lymphomas, graft-versus-host diseases, and autoimmune diseases by administering the immunotoxin anti-CD3-CRM9.

SUMMARY OF THE INVENTION

It is a general object of this invention to provide an immunotoxin.

It is a specific object of this invention to provide an immunotoxin.

It is a further object of the invention to provide a method of treating T cell leukemias or lymphomas.

It is a further object of the invention to provide a method of treating autoimmune diseases.

In one embodiment, the invention provides a method of treating an autoimmune disease in an animal comprising administering to the animal an antibody-CRM9 conjugate which routes by the anti-CD3 pathway, or derivatives thereof, under conditions such that the autoimmune disease is treated.

In another embodiment, the invention provides an anti-Vβ-CRM9 immunoconjugate.

In a further embodiment, the invention provides a method of treating T cell leukemias or lymphomas in an animal comprising administering to the animal an antibody-CRM9 conjugate which routes by the anti-CD3 pathway, or derivatives thereof, under conditions such that the T cell leukemias or lymphomas are treated.

A further embodiment provides a method of treating graft-versus-host disease in an animal, comprising administering to the animal a non-toxic mutant of diphtheria toxin followed by an antibody-CRM9 conjugate which routes by the anti-CD3 pathway, or derivatives thereof under conditions such that the graft-versus-host disease is treated.

A still further embodiment provides a method of treating an autoimmune disease in an animal comprising administering to the animal a non-toxic mutant of diphtheria toxin followed by an antibody CRM9 conjugate which routes by the anti-CD3 pathway, or derivatives thereof, under conditions such that the autoimmune disease is treated.

The invention also provides a method of treating acquired immunodeficiency syndrome in an animal, comprising administering to the animal a non-toxic mutant of diphtheria toxin followed by an antibody-CRM9 conjugate which routes by the anti-CD3 pathway, or derivatives thereof under conditions such that acquired immunodeficiency syndrome is treated.

Further objects and advantages of the present invention will be clear from the description that follows.

DETAILED DESCRIPTION OF THE INVENTION

Figure 1:
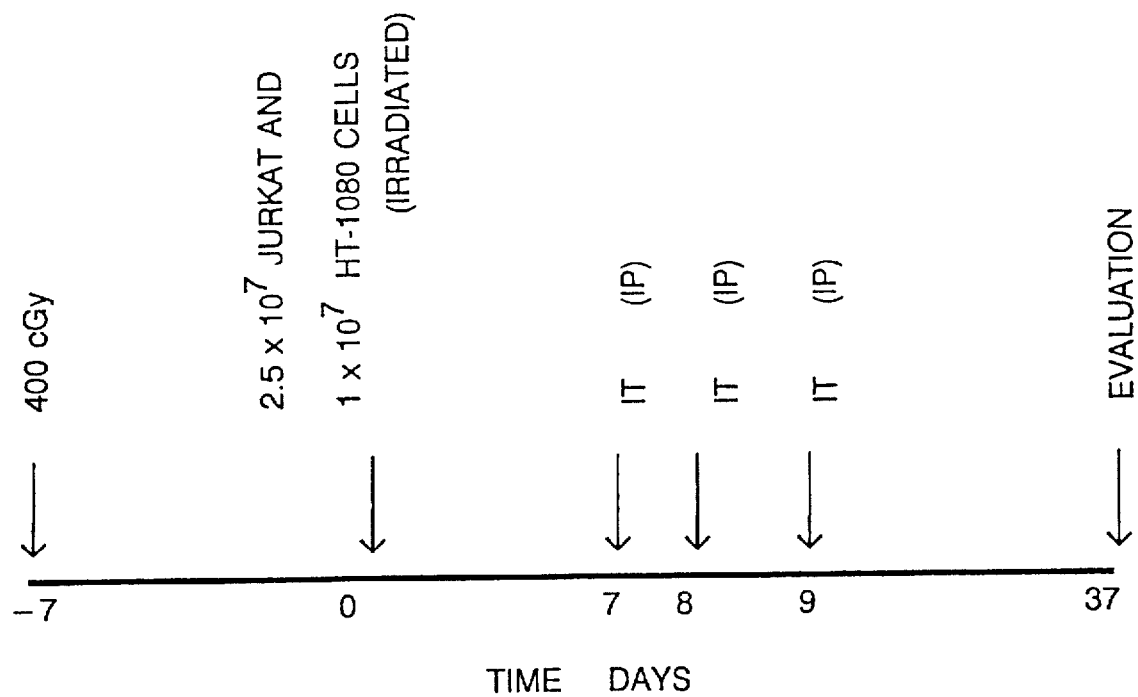
FIG. 1. Nude mice bg/nu/xid maintained in a semi-sterile environment are preconditioned with 400 cGy whole body ¹³⁷CS γ radiation on day −7. On day 0, 2.5×10⁷ Jurkat cells (human T cell leukemia CD3+, CD4+, CD5+) are injected subcutaneously with 1×10⁷ HT-1080 feeder cells (human sarcoma) which have received 6000 cGy. Jurkat cells were passaged every other week in mice as subcutaneous tumors and dissociated by collagenase/dispase prior to inoculation. This cell population exhibits a 40% inhibition of protein synthesis after 5 hours exposure to 10⁻¹¹M anti-CD3-DT. Clones isolated from this population by infinite dilution exhibit varying sensitivity to anti-CD3-DT (4 less sensitive, 3 more sensitive) corresponding to a 1.5 log variation in dose response curves. Immunotoxin treatment is given by intraperitoneal injection starting on day 7 when the tumor is visibly established. Evaluation takes place on day 37.

The present invention relates to an immunotoxin. In one embodiment, the present invention relates to an immunotoxin comprising anti-CD3-CRM9 or derivatives thereof. The design of successful derivatives of anti-CD3-CRM9 depend upon understanding how the unique concentration of anti-CD3-CRM9 achieves its biological effect. The toxin moiety CRM9 retains its toxic function, and membrane translocation function to the cytosol in full amounts. The loss in binding function located in the C terminus of the protein diminishes systemic toxicity by reducing binding to non-target cells. The routing function normally supplied by the toxin binding function is supplied by the targeting antibody anti-CD3. The essential routing pathway is (1) localization to coated pits for endocytosis, (2) escape from lysosomal routing, and (3) return to the plasma membrane. Any antibody which can route in this manner will be effective with CRM9, irrespective of the epitope to which the antibody is directed. Thus, a wide variety of cell types can in principle be targeted. When antibodies dissociate from their receptors due to changes in receptor configuration induced in certain receptors as a consequence of endosomal acidification, they enter the lysosomal pathway. This can be prevented or minimized by directing the antibody towards an ecto-domain epitope on the same receptor which is closer to the plasma membranes (Ruud, et al. (1989) *Scand. J. Immunol.* 29:299; Herz et al. (1990) *J. Biol. Chem.* 265:21355). Other DT binding site mutants can be used to form derivatives by changing amino acids in the C-terminus which can reduce the binding function as long as the translocation function is maintained.

An example of a series of derivatives which is likely to be effective are antibody-CRM9 conjugates directed at unique Vα and Vβ gene segment products of the T cell receptor. Some of these epitopes appear to be biased towards specific autoimmune processes. Such conjugates should be useful in specific autoimmune diseases (Kappler et al. (1987) *Cell* 49:263; Urban et al. (1988) *Cell* 54:577).

Relatedly, the invention provides an anti-Vβ-CRM9 immunoconjugate such as anti-Vβ₁₂-CRM9. Also provided is an anti-Vα-CRM9 immunoconjugate. Both of the conjugates can be placed in a pharmaceutically acceptable carrier for administration to a subject. Both acid-cleavable and non-cleavable protein cross-linking reagents can be used in the construction of antibody-diphtheria toxin binding-site mutant conjugates like anti-CD3-CRM9 (Neville et al. (1989) *J. Biol. Chem.* 264:14653–14661); preferred are non-cleavable crosslinkers, such as bismaleimidohexane and m-maleimidobenzoyl-N-hydroxysuccinimide ester. The synthesis of acid-cleavable protein cross-linking reagents based on orthoester, acetal, and ketal functionalities has been described (Srinivasachar and Neville (1989) *Biochemistry* 28:2501–2509). The unique feature of these functionalities is that their observed hydrolytic rate constants increase 10-fold for each drop in pH, a consequence of specific $H_3O^+$ catalysis leading to a carbonium ion intermediate (Cordes and Bull (1974) *Chem. Rev.* 74:581–603). Moreover, these functionalities are resistant to base catalysis permitting manipulation and storage at alkaline pH. The cross-linking reagents react with proteins via heterobifunctional groups (maleimide and N-hydroxysuccinimide ester) or homobifunctional groups (bis-maleimide). The maleimide cross-linking is accomplished by prior protein thiolation with iminothiolane. Cross-linked proteins exhibit first-order dissociation under acid conditions. The $t_{1/2}$ at pH 5.5 varies between 0.1 and 130 h for a series of six different cleavable cross-linkers (Srinivasachar and Neville (1989) *Biochemistry* 28:2501–2509).

The CRM9 conjugates of the invention can be expected to be effective as immunotoxins, because the relevant parameters are known. The relevant binding constants, number of receptors and translocation rates for humans have been determined and used. Binding values for anti-CD3-CRM9 for targeted and non-targeted cells in vitro are described above at page 2. Rates of translocation for the anti-CD3-CRM9 conjugate to targeted and non-targeted cells in vitro are described in references cited at page 2 (Greenfield et al. (1987) *Science* 238:536; Johnson et al. (1988) *J. Biol. Chem.* 263:1295; Johnson et al. (1989) *J. Neurosurg.* 70:240; and Neville et al. (1989) *J. Biol. Chem.* 264:14653). The rate limiting translocation rate to targeted cells in vitro is recited at page 5, wherein it is shown that the conjugate is translocated to about 40% of the target cells present as measured by inhibition of protein synthesis in about 40% of cells. Inhibition of protein synthesis is complete in cells into which the conjugate translocates.

Parameters determined in in vivo studies in nude mice include the following: Tumor burden is described in Example 1 as a constant mass equal to 0.1% of body weight; the receptor number and variation of receptor number are described in Example 3; "favorable therapeutic margin" is defined as an in vivo target cell 3 log kill at 0.5 MLD (minimum lethal dose) comparison of efficacy with an established treatment of 0.5 MLD immunotoxin equivalent (group 1) to a radiation dose of 500–600 cGy (groups 8 and 9).

The parameters determined in vitro allowed the prediction of success in the in vivo nude mouse study. The prediction of in vivo success was verified by the data in Examples 3–4. Using the target cell number from the mouse study as being equivalent to the local T cell burden in a monkey or man successful T cell ablation and immunosuppression in monkeys could be predicted. This prediction has been verified by the monkey data in Examples 5 and 7–8. Using the same parameters, a scientist skilled in this field can make a prediction of success in humans with confidence, because these parameters have been previously shown to have predictive success.

In another embodiment, the present invention relates to a pharmaceutical composition comprising anti-CD3-CRM9 or derivatives thereof in an amount effective to treat T cell leukemias or lymphomas which carry the CD3 epitope, graft-versus-host disease or autoimmune diseases, and a pharmaceutically acceptable diluent, carrier, or excipient. One skilled in the art will appreciate that the amounts to be administered for any particular treatment protocol can readily be determined. Suitable amounts might be expected to fall within the range of 0.01 to 1.0 mg (CRM9 content) per kg of body weight.

Thus, one embodiment of the invention provides a method of treating an autoimmune disease in an animal comprising administering to the animal an antibody-CRM9 conjugate which routes by the anti-CD3 pathway, or derivatives thereof, under conditions such that the autoimmune disease is treated. Examples of such conjugates include anti-Vβ-CRM9 and anti-Vα-CRM9. In one embodiment, the anti-Vβ-CRM9 is anti-Vβ$_{12}$-CRM9 and the disease is human immunodeficiency virus disease or the Acquired Immunodeficiency Syndrome (AIDS). Other Vα and Vβ targets associated with particular autoimmune diseases exist. For example, pulmonary sarcoidosis showed increased usage of the Vβ$_8$ subset in blood and lung lymphocytes (Moller et al. (1988) *J. Clin. Invest.* 82:1183–1191). In multiple sclerosis, preferential use of the Vβ$_{5.2}$ subset in brain plaque lesions has been identified and rearrangements of Vα$_{1,2,7,8,and\ 10}$ were also prominent (Oksenberg et al. (1993) *Nature* 362:68–70).

A further embodiment of the invention provides a method of treating T cell leukemias or lymphomas in an animal comprising administering to the animal an antibody-CRM9 conjugate which routes by the anti-CD3 pathway, or derivatives thereof, under conditions such that the T cell leukemias or lymphomas are treated. For example, the antibody-CRM9 conjugate used in any of the methods herein can be an anti-Vβ-CRM9 such as anti-Vβ$_8$-CRM9. In addition, the antibody-CRM9 conjugate can be an anti-Vα-CRM9.

A method of treating acquired immunodeficiency syndrome in an animal, comprising administering to the animal a non-toxic mutant of diptheria toxin followed by an antibody-CRM9 conjugate which routes by the anti-CD3 pathway or derivatives thereof under conditions such that the acquired immunodeficiency syndrome is treated is provided. Anti-Vβ$_{12}$ is a liekly conjugate for use in this method.

A further embodiment is a method of treating T cell leukemias or lymphomas in an animal comprising administering to the animal a non-toxic mutant of diphtheria toxin followed by an antibody-CRM9 conjugate which routes by the anti-CD3 pathway, or derivatives thereof, under conditions such that the T cell leukemias or lymphomas are treated.

The non-toxic mutant of diphtheria toxin for use in the above method can be CRM197. CRM197 is a non-toxic mutant of DT, having a point mutation in the enzymatic chain. However, it has the full antigenic properties of DT and CRM9, and is used for immunization (Barbour et al. 1993. *Pediatr Infect. Dis. J.* 12:478–84). Other non-toxic DT mutants that can be used in the present method will share the characteristic of totally lacking A chain enzymatic activity. The purpose of administering the non-toxic toxin is to bind preexisting anti-CRM9 anti-DT antibodies in a subject and compete with their effect and/or induce their removal from the circulation. This substantially avoids any host immune response to the immunotoxin that might interfere with the activity of the imunotoxin.

The non-toxic DT mutant is administered prior to the administration of immunotoxin. For example, non-toxic mutant can be administered at least 5 minutes prior to the immunotoxin. A range of doses of the non-toxic mutant can be administered. For example, an approximately 10 to 100 fold excess of non-toxic mutant over the CRM9 content of the immunotoxin to be administered can be administered by I.V. route.

A H1 histamine blocking agent such as Benadryl or Tagevil can be administered I.V. prior to administering the non-toxic mutant to minimize any possibility of an anaphylactic reaction. No evidence of anaphylactic reaction was noted in the primate experiments described in the Examples. However, the H1 histamine blocker can be administered as a precaution with no significant disadvantage.

In a further embodiment, the present invention relates to a method of treating T cell leukemias or lymphomas which carry the CD3 epitope in an animal comprising administering to an animal anti-CD3-CRM9 or derivatives thereof under conditions such that the leukemias or lymphomas regress. Appropriate concentrations and dosage unit sizes can be readily determined by one skilled in the art.

In another embodiment, the invention relates to a method of treating an immune system disorder not involving T cell proliferation which is amenable to T cell suppression. In a specific embodiment, the present invention relates to a method of treating graft-versus-host disease (GVHD) in an animal comprising administering to an animal anti-CD3-CRM9 or derivatives thereof under conditions such that the symptoms of the graft-versus-host disease improve. GVHD is a morbid complication of bone marrow transplantation which is often performed as anti-leukemia/lymphoma therapy. GVHD is caused by circulating donor T cells within the host which are acquired in bone marrow grafts unless specifically depleted prior to grafting (Gale and Butturini (1988) *Bone Marrow Transplant* 3:185; Devergie et al. (1990) ibid 5:379; Filipovich et al. (1987) *Transplantation* 44). Successful donor T cell depletion techniques have been associated with a higher frequency of graft rejection and leukemia relapses (Gale and Butturini (1988) *Bone Marrow Transplant* 3:185; Devergie et al. (1990) ibid 5:379; Filipovich et al. (1987) *Transplantation* 44). Therefore, the donor T cells appear to aid engraftment and to provide a graft-versus-leukemia effect as well as causing GVHD. Because the T cell burden following bone marrow transplantation is low for the first 14 days (<10% of normal) the log kill of donor T cells would be proportionally enhanced (Marsh and Neville (1987) *Ann. N.Y. Acad. Sci.* 507:165; Yan et al., submitted; Gale and Butturini (1988) *Bone Marrow Transplant* 3:185; Devergie et al. (1990) ibid 5:379; Filipovich et al. (1987) *Transplantation* 44). It is expected that donor T cells can be eliminated at set times during the early post transplantation period using the present method. In this way the useful attributes of grafted T cells might be maximized and the harmful effects minimized.

Also provided is a method of treating graft-versus-host disease in an animal by administering to the animal a non-toxic mutant of diphtheria toxin followed by an antibody-CRM9 conjugate which routes by the anti-CD3 pathway, or derivatives thereof under conditions such that the graft-versus-host disease is treated. This method can use the antibody-CRM9 conjugates and non-toxic DT mutants described herein with the dosages and modes of administration as described herein or otherwise determined by the practitioner.

In a further embodiment, the present invention relates to a method of treating autoimmune diseases in an animal comprising administering to the animal anti-CD3-CRM-9 or derivatives thereof under conditions such that the symptoms of the autoimmune disease improve. A further method of treating an autoimmune disease in an animal comprises administering to the animal a non-toxic mutant of diphtheria toxin followed by an antibody CRM9 conjugate which routes by the anti-CD3 pathway, or derivatives thereof, under conditions such that the autoimmune disease is treated.

In one preferred embodiment, AIDS is treated. Radiation induced T cell ablation with concomitant high dose zidovudine therapy followed by bone marrow transplantation has been reported to eradicate HIV-1 infection in one case (Holland et al. (1989) *Ann. Int. Med.* 111:973). Cyclophosphamide, a T cell suppressive reagent, has been shown to be beneficial in treating murine AIDS (Simard and Joliceur (1991) *Science* 251:305). Anti-CD3-CRM9 provides extensive T cell ablation without the requirement of bone marrow reconstitution.

Hemi-immunotoxins (MAbs conjugated to ricin A chain) have been used clinically as T cell suppressants for the treatment of GVHD, rheumatoid arthritis and T cell leukemia (Program and Abstracts 2nd Int. Symposium on Immunotoxins, June 1990, Lake Buena Vista, Fla.; Byers et al. (1990) *Blood* 75:1426). Some positive effects have been noted. The immunotoxin described here is more toxic on a weight basis than hemi-immunotoxins, but at tolerated doses exhibits an apparent log kill of targeted cells at target cell burdens encountered clinically. This constitutes a favorable therapeutic margin. Most human sera contain anti-DT neutralizing antibodies from childhood immunization (Johnson et al. (1989) *J. Neurosurg.* 70:240). To compensate for this the therapeutic dose of anti-CD3-CRM9 can be appropriately raised without affecting the therapeutic margin. Alternatively, a non-toxic DT mutant reactive with neutralizing antisera, such as CRM197, can be administered prior to the conjugate.

The present invention will be illustrated in further detail in the following non-limiting examples.

EXAMPLE 1

Establishment of Tumors

The experimental design of the studies that give rise to the present invention was dictated by the goal of having an animal model as closely relevant to human in vivo tumor therapy as possible. In order to minimize the host killer cell immune response, bg/nu/xid strain of nude mice were used (Kamel-Reid and Dick (1988) *Science* 242:1706). The human T cell leukemia cell line, Jurkat, was chosen because of previous studies with this line and its relatively normal average complement of CD3 receptors (Preijers et al. (1988) *Scand. J. Immunol.* 27:553). The line was not cloned so that receptor variation among individual cells existed (FIG. 1 legend). A scheme was developed whereby well established tumors of constant mass equal to 0.1% of body weight ($\approx 4 \times 10^7$ cells) could be achieved 7 days after inoculation of Jurkat cells (see FIG. 1 and Dillman et al. (1988) *Cancer Res.* 15:5632). This required prior irradiation and inoculation with lethally irradiated helper feeder cells (see FIG. 1 and Dillman et al. (1988) *Cancer Res.* 15:5632).

EXAMPLE 2

Guinea Pig Studies

Immunotoxin toxicity studies were performed in guinea pigs, an animal (like humans) with a high sensitivity to diphtheria toxin (mice are highly resistant to diphtheria toxin). Therapy of CRM9 conjugates was set at ½ the guinea pig minimum lethal dose. In this study, minimum lethal dose (MLD) is defined as the minimum tested dose which results in both non-survivors and survivors over a 4 week evaluation period. All animals survive when a MLD is reduced by 0.5. MLD was evaluated in guinea pigs (300–1000 g) by subcutaneous injection. The following MLDs were found and are listed as μg of toxin/kg body weight; DT, 0.15; CRM9, 30; anti-CD5-DT (cleavable), 0.65; anti-CD5-CRM9 (non-cleavable), 150. Finally, the therapeutic efficacy of the immunotoxin treatment in producing tumor regressions was compared to graded doses of whole body irradiation which resulted in similar tumor regressions.

EXAMPLE 3

Comparison of Immunotoxins

Several types of immunotoxins were compared in this study. They were synthesized as previously described by thiolating both the monoclonal antibody moiety and the toxin moiety and then crosslinking the bismaleimide crosslinkers (Neville et al. (1989) *J. Biol. Chem.* 264:14653). Purification was performed by size exclusion HPLC columns and fractions containing 1:1 toxin:antibody mol ratios were isolated for these studies. Conjugates made with an acid-labile crosslinker bismaleimidoethoxy propane were compared with a non-cleavable, bismaleimidohexane. Conjugates made with this cleavable crosslinker have been shown to hydrolyze within the acidifying endosome releasing free toxin moieties with half-times of hydrolysis measured at pH 5.5 of 36 min (Neville et al. (1989) *J. Biol. Chem.* 264:14653).

The results of this study are tabulated in Table I. Non-treatment groups such as group 10, groups treated with anti-CD5 immunotoxins (groups 5 and 6), and group 4 treated with a mixture of anti-CD3 and CRM9 did not show regression. The vascularized tumor nodules that weighed 20 mg on day 7 grew to between 1.5 to 7.8 g on day 37 and weighed between 7.9 and 11.6 on day 56. No late spontaneous regressions were noted. In contrast, group 1 consisting of treatment with anti-CD3-CRM9 non-cleavable conjugate (NC) given at 25 μg/kg on days 7, 8, and 9 (see FIG. 1 time line) showed only 1 tumor out of 6 by day 37. Some of the remaining animals were subject to autopsy and they failed to reveal residual tumor or even scaring. Tumors identified as regressed on day 37 by superficial inspection did not reappear during the course of the study (56 days).

TABLE I

IMMUNOTOXIN AND RADIATION TREATMENT ON SUBCUTANEOUS HUMAN T CELL TUMORS (JURKAT) IN NUDE MICE

| Group | Treatment | Dose (intraperitoneal) | Animals Bearing Tumors At Day 37/Group Animals | % Tumor Regressions |
|---|---|---|---|---|
| 1 | Anti-CD3 – CRM9 (NC)* | 25 μg/kg. × 3d | 1/6 | 83 |
| 2 | Anti-CD3 – CRM9 (NC) | 19 μg/kg. × 2d | 1/4 | 75 |
|   | Anti-CD5 – CRM9 (C) | 19 μg/kg. × 2d | | |
| 3 | Anti-CD3 – CRM9 (C) | 25 μg/kg. × 3d | 2/4 | 50 |
| 4 | Anti-CD3 + CRM9 | 25 μg/kg. × 3d | 4/4 | 0 |

TABLE I-continued

IMMUNOTOXIN AND RADIATION TREATMENT ON SUBCUTANEOUS HUMAN
T CELL TUMORS (JURKAT) IN NUDE MICE

| Group | Treatment | Dose (intraperitoneal) | Animals Bearing Tumors At Day 37/Group Animals | % Tumor Regressions |
|---|---|---|---|---|
| 5 | Anti-CD5 – CRM9 (C) | 25 µg/kg. × 3d | 5/5 | 0 |
| 6 | Anti-CD5 – DT (NC) | 25 µg/kg. × 1d | 9/9 | 0 |
| 7 | γradiation $^{137}$Cs | 400 cGy | 2/2 | 0 |
| 8 | γradiation $^{137}$Cs | 500 cGy | 3/6 | 50 |
| 9 | γradiation $^{137}$Cs | 600 cGy | 0/2[b] | 100 |
| 10 | None | | 6/6 | 0 |

[a]Anti-CD3 refers to the monoclonal antibody UCHT1 and was purchased from Oxoid USA, Inc.
Anti-CD5 refers to the monoclonal antibody T101 and was a gift from Hybritech (San Diego). NC and
C refer, respectively, to non-cleavable and cleavable conjugates.
[b]These animals were evaluated on days 10 and 13 at the time of death from radiation sickness.

The cleavable crosslinker confers no therapeutic advantage to anti-CD3-CRM9 immunotoxins and may be less effective (group 3). Cleavable crosslinkers confer some advantage with anti-CD5-CRM9 conjugate in vitro (5) but had no effect in this in vivo system (group 5), and lacked significant potentiating effect when administered with anti-CD3-CRM9 (group 2). The cleavable crosslinker conferred a marked therapeutic advantage to anti-CD5 wild type toxin conjugates and tumor regressions were achieved. However, in these cases the guinea pig toxic dose was exceeded. A single dose on day 7 of cleavable anti-CD5-DT at 6 µg/kg produced 8/10 tumor regressions while a cleavable conjugate made with an irrelevant antibody (OX8) produced no regressions (4/4). However, this dose exceeded the guinea pig MLD by 9 fold. A rescue strategy was tried in which the above conjugate dose was given intravenously followed by DT antitoxin 4 hours later (also intravenously). The 4 hr rescue could not raise the MLD above 0.65 µg/kg. The 1 hr rescue could not raise the MLD above 0.65 µg/kg. The 1 hr rescue raised the MLD to 36 µg/kg, however, there were no tumor regressions in 10 mice receiving 21.5 µg/kg of the cleavable anti-CD5-DT conjugate.

In groups 7–9 increasing single doses of whole body radiation (102 cGy/min) were given to animals bearing 3×3×5 mm tumors. At 400 cGy no complete regressions occurred. At 500 cGy 50% complete tumor regressions occurred. At 600 cGy 100% regression was achieved as judged on day 10 and 13 when the animals died from radiation sickness. (Groups 7–9 did not receive prior radiation and tumor takes were less than 100%). It appears that the 75 µg/kg anti-CD3-CRM9 (NC) immunotoxin is equal in therapeutic power to between 500 and 600 cGy of radiation.

EXAMPLE 4

Estimation of Cell Kill

The actual cell kill achieved by the radiation and the immunotoxin can be estimated by assuming radiation single hit inactivation kinetics along with a $D_{37}$ value for the radiation. A value for $D_{37}$ of 70–80 cGy with n=1.2–3 is not unreasonable for a rapidly dividing helper T cell. $D_{37}$ is the dose of radiation which reduces the fraction of surviving cells to 1/e as extrapolated from the linear portion of the log survivors vs. dose curve and n is the intercept at 0 dose (Anderson and Warner (1976) in Adv. Immunol., Academic Press Inc., 24:257). At a dose of 550 cGy the fraction of surviving cells is calculated to be about $10^3$. Since a majority of tumors completely regress at this dose we estimate that both therapies are producing an approximate 3 log kill. (The remaining cells, $4×10^7×10^3=4×10^4$ cells apparently cannot maintain the tumor, i.e., the in vivo plating efficiency is low, a fairly typical situation in the nude mouse xenograft system.) The reliability of this 3 log kill estimate has been verified by determining the tissue culture plating efficiency by limiting dilution of 7 day established Jurkat tumors (following dispersal) and tumors exposed 18 hours earlier in vivo to 600 cGy. Plating efficiencies were 0.14 and $1.4×10^4$, respectively. (Plating efficiency is the reciprocal of the minimum average number of cells per well which will grow to form one colony.

It should be emphasized that with high affinity holo-immunotoxins the cell kill is inversely proportional to the target cell number. This presumably occurs because receptors are undersaturated at tolerated doses and free conjugate concentration falls with increasing target cell burden (Marsh and Neville (1987) Ann. N.Y. Acad. Sci. 507:165; Yan et al. (1991) Bioconjugate Chem. 2:207). To put this in perspective, the tumor burden in this study is almost equal to the number of T cells in a mouse ($\approx 10^8$). It can be expected that a tolerated dose of anti-CD3-CRM9 immunotoxin can achieve an in vivo 3 log depletion of a normal number of CD3 positive T cells.

EXAMPLE 5

Cell Depletion in Rhesus Monkeys Induced by FN18-CRM9

FN18-CRM9 conjugate

Conjugation of anti-Vβ and anti-Vα IgG monoclonal antibodies to CRM9 is performed by the same methods used to conjugate anti-CD3 to CRM9 using a non-cleavable linker such as bismaleimidohexane and previously described in detail (Neville et al. (1988) J. Biol. Chem. 264:14653–61). The monoclonal antibody FN18 is the monkey equivalent of the human anti-CD3 (UCHT1) and is known to bind the same CD3 receptor epitopes (ε and γ) as bound by the human CD3 antibody and is the same isotype as the human CD3 antibody. Thus, in terms of the parameters relevant for predicting successful T cell depletion, the present CD3-CRM9 conjugate and FN18-CRM9 are expected to have the same activity.

Administration

Conjugates can be administered as an I.V. bolus in a carrier consisting of 0. 1M $Na_2SO_4$+0.01M phosphate buffer, pH 7.4 plus 1 part in 50 of serum previously obtained from the subject. The dose schedule is every other or third day for 3 to 6 days. The total dose is preferably from 25 to 200 micrograms of toxin per kg of body weight.

The actual dose of FN18-CRM9 used was equal to 0.167 of the minimum lethal dose (MLD) in guinea pigs. Since the estimation of the MLD was performed in an animal lacking an immunotoxin target cell population (guinea pigs), the true MLD of FN18-CRM9 and anti-CD3-CRM9 is expected to be higher in monkeys and humans than in guinea pigs.

T Cell Kill

Helper T cell (CD4+ cells) numbers in peripheral blood fell dramatically after the initial administration of FN18-CRM9 in two rhesus monkeys. T cell counts began to rise by day 4 (sampled just prior to the second dose of FN18-CRM9). On day 5 in monkey 8629, CD4+ cells were depressed below the limit of detection (<50 cellS/mm$^3$) Cells remained below or equal to 200/mm$^3$ out to day 21. This low level of CD4+ cells is associated with profound immunodeficiency in humans and in monkeys (Nooij and Jonker (1987) Eur. J. Immunol. 17:1089–1093). The remarkable feature of this study is the long duration of helper T cell depletion (day 21) with respect to the last administration of immunotoxin (day 4) since intravenously administered immunotoxins were cleared from the vascular system with half-lives <9 hours (Rostain-Capaillon and Casellas (1990) Cancer Research 50:2909–2916), the effect outlasting circulating immunotoxin. This is in contrast to T cell depletion induced by unconjugated anti-CD3 antibodies (Nooij and Jonker (1987) Eur. J. Immunol. 17:1089–1093).

In monkey 1WS the second dose of conjugate only appeared to result in a diminished rate of CD4+ cell recovery. However, CD4+ cells were still fewer than normal at day 21. The blunted response of monkey 1WS to the second dose of immunotoxin was found to be due to a preexisting immunization of this animal to the toxin. Monkey 1WS had a significant pre-treatment anti-diphtheria toxin titer as revealed by a Western blot assay. This titer was markedly increased at day 5, indicative of a classic secondary response. In contrast, monkey 8629 had no detectable pre-treatment titer and only a trace titer by day 5 and a moderate titer by day 28.

The specificity of FN18-CRM9 toward T cells can be seen by comparing the total white blood cell (WBC) count in the same two monkeys. WBCs fell, but only to 45% of baseline value on day 2 compared to 6% of baseline values for the CD4+ T cell subset. Most of the fall in WBC values can be accounted for by the T cell component of the WBC population (≈40%). However, B cells are initially depleted after FN18-CRM9 although these cells recover more quickly. FN18 is an IgG, isotype and as such is known to bind to Fc$_{II}$ receptors present on B cells and macrophages with low affinity. The FN18-CRM9 depletion of B cells indicates that significant interactions between the Fc portion of the FN18 antibody and B cells is taking place.

The peripheral T cell depletion induced by unconjugated FN18 at a dose known to produce immunosuppression 0.2 mg/kg/day (Nooij and Jonker (1987) Eur. J. Immunol. 17:1089–1093) was compared to the immunotoxin FN18-CRM9 administered at ⅙th the FN18 dose. Peripheral CD4+ T cell depletion is more pronounced and more long-lasting with the conjugate. The demonstration that FN18-CRM9 reduces peripheral helper T cell subset (CD4+) to levels less than or equal to 200 cell/mm$^3$ for a period as long as 21 days demonstrates that this immunotoxin and its anti-human analogs are effective immunosuppressive reagents.

The demonstration that FN18-CRM9 is a potent agent for inducing T cell depletion in non-human primates demonstrates that an anti-human homolog of FN18-CRM9, UCHT1-CRM9 (Oxoid USA, Charlotte, N.C.) for example, is a potent agent for inducing T cell depletion in humans.

The Fc binding region of anti-TCR/CD3 monoclonals may or may not be needed to induce T cell depletion when the anti-TCR/CD3 monoclonals are conjugated to CRM9. The Fc$_{II}$ binding regions can be removed, for example, by forming the conjugates with F(ab')$_2$ derivatives as is indicated in the literature (Thorpe et al. (1985) J. Nat'l. Cancer Inst. 75:151–159). In addition, anti-TCR/CD3 IgA switch variants such as monoclonal antibody T3.A may be used (Ponticelli et al. (1990) Transplantation 50:889–892). These avoid rapid vascular clearance characteristic of F(ab')$_2$ immunotoxins. F(ab')$_2$ and IgA switch variants of anti-TCR/CD3-CRM9 immunotoxins are therefore derivative anti-TCR/CD3 immunotoxins. These derivatives will avoid the B cell interaction noted and can increase specificity. However, IgG$_{2a}$ switch variants will maximize T cell activation through the Fc$_{/}$. receptor and may be useful in certain situations where T cell activation aids immunotoxin induced toxicity.

General methods to make antibodies lacking the Fc region or to make antibodies which are humanized are set forth in Harlow and Lane, Antibodies: A Laboratory Manual, Cold Spring Harbor Laboratory, Cold Spring Harbor, N.Y., 1988. Thus, as used in the claims, antibody can mean the entire antibody or any portion of the antibody sufficient for specific antigen or receptor binding.

EXAMPLE 6

Treatment of Autoimmune Diseases Using Other Antibody-CRM9 Conjugates which Route by the Anti-CD3 Pathway Since receptor recycling is a requirement for effective CRM9 based immunotoxins and since TCR/CD3 recycles as a unit, antibodies directed at other epitopes on TCR/CD3 will constitute effective derivatives, in particular antibodies directed at the approximately 50 Vβ subset families or the approximately equal number Vα subsets can be used to conjugate CRM9 and ablate specific Vβ or Vα subsets in vivo. In addition, in some cases it may be possible to develop specific monoclonal antibodies reacting with unique rearrangements of either the Vα or Vβ subset families.

The advantage of targeting the specific Vβ or Vα subset (s) as opposed to the entire T cell population is twofold: (1) Elimination of a Vβ subset does not create a generalized immunodeficiency, only a hole in the immune repertoire is generated. Therefore, the ability to ward off most infections and maintain immune surveillance of most malignant transformations would remain intact. (2) Immunotoxin log kill increases linearly as the target cell burden decreases, assuming dose is unchanged. A 50-fold increase in log kill can be obtained as the target is changed from the entire set of T cells to a single Vβ subset. However, due to (1) the high affinity of binding of these immunotoxins, (2) the very low total dose given which is below target cell receptor saturation and (3) the irreversible nature of the endocytotic process, the target cells deplete the effective dose and this depletion decreases as target burden decreases. Since the log kill is exponential in effective dose, much higher increases in log kill than 50-fold on changing the target from T cells to a Vβ subset can occur. The expected increase in log kill will only occur if the immunotoxin is specific for the defined target. Extraneous interactions with other cell types via the antibody Fc piece is preferably eliminated.

Because HIV has been shown to preferentially infect one (Vβ$_{12}$) or a few of the 20 Vβ subset families providing a small T cell reservoir of HIV replication, and because HIV infection apparently involves an unknown superantigen, CRM9 based immunotoxins directed at these specific Vβ subsets such as anti-Vβ$_{12}$-CRM9 can reduce the HIV virus load. In addition, total ablation of a Vβ subset in the presence of an endogenous superantigen can lead to long-term ablation of the subset since maturing T cells are negatively selected in the presence of endogenous superantigens. Since the specific Vβ subset responding to the superantigen is eliminated, infection cannot take place.

The two strategies that can be utilized for using anti-Vβ$_{12}$-CRM9 immunotoxins to treat HIV-infections are (1) treatment depleting the susceptible Vβ subset to an extent where continued infection cannot be maintained and (2) treatment to the extent that all or nearly all of the VDβ$_{12}$ subset is eradicated.

Anti-human Vβ monoclonal antibodies such as S5–11 (anti-Vβ$_{12}$) are available (T Cell Sciences, Cambridge, Mass.) and can be conjugated to CRM9 by standard methodologies.

Briefly, as in Example 5, conjugation of anti-Vβ and anti-Vα IgG monoclonal antibodies to CRM9 is performed by the same methods used to conjugate anti-CD3 to CRM9 using a non-cleavable linker such as bismaleimidohexase and previously described in detail (Neville et al. (1988) *J. of Biol. Chem.* 264:14653–61).

Conjugates can be administered as an I.V. bolus in a carrier consisting of 0.1M Na$_2$SO$_4$+0.01M phosphate buffer, pH 7.4 plus 1 part in 50 of serum previously obtained from the patient. The dose schedule is every other or third day for 3 to 6 days. The total dose is preferably from 25 to 200 micrograms of toxin per kg of body weight, but may be increased if anti-diphtheria toxin antibodies are present in the patient's sera in significant amounts.

Other Vβ or Vα subsets which may be found to be associated with HIV infection can be treated in the same manner described herein by conjugating the CRM9 to the antibody specifically reactive with the appropriate Vβ or Vα subset.

EXAMPLE 7

T Cell Depletion and Immunosuppression in Monkeys Using the Immunotoxin Anti-CD3-CRM9

CRM9 is a diphtheria toxin (DT) binding site mutant and forms the basis of the anti-T cell immunotoxin anti-CD3-CRM9. This immunotoxin has been constructed against human and rhesus T cells and has shown above to kill 3 logs of human T cells in a nude mouse xenograft system. The present example demonstrates a 2 log kill of T cells in rhesus monkey lymph nodes that is also shown to produce prolongation of skin allograft rejection in monkeys.

Humans are immunized against diphtheria toxin by exposure to DPT vaccines in childhood. This long lasting immunity may interfere with the efficacy of DT based immunotoxins. Many monkeys are immunized against DT by natural exposure to toxin producing Corynebacterium. The present method addresses any potential interference of pre-existing DT antibodies with the activity of the present immunotoxins.

ELISA

ELISA assays were performed in order to determine the levels of anti-DT titers existing in 9 individuals in a population ages 27 to 55. There were 3 individuals with titers of 1:100 (low) and 6 with titers of 1:1000 (moderate).

Rhesus monkeys were screened by the same assay and a 1:1000 titered monkey was selected.

Administration of Non-Toxic Diphtheria Toxin Mutant

Monkeys were treated by I.V. route 5 min prior to the immunotoxin dose with a 100 fold excess of CRM197 over the CRM9 content of the immunotoxin to be administered. Just prior to administering CRM197, a H1 histamine blocking agent such as Benadryl or Tagevil was given I.V. to minimize any possibility of an anaphylactic reaction (for Benadryl 4 mg/kg). No histaminic reaction was detected.

Anti-CD3-CRM9 was given at a total dose between 0.1 and 0.2 mg/kg (toxin weight) in 3 equally divided doses (approximately 0.033 mg/kg) on 3 consecutive days. In these monkeys, the total dose of immunotoxin was 0.1 mg/kg.

Table I shows a comparison of the efficacy of anti-CD3-CRM9 in monkeys by comparing the decrease in the lymph node T/B cell ratio (a measure of lymph node T cell depletion) and the immunosuppressive effect of the immunotoxin as judged by prolongation of mismatched skin graft survival. Effects on the survival of skin grafts is a clear indicator of the general effect a given treatment has on the subject's immune system.

The monkey with the preexisting anti-DT titer that was pretreated with CRM197 shows the same level of T/B cell inversion as in the negative titered monkey. Skin graft survival was significantly prolonged over the titered monkey treated without CRM197. The failure to achieve a prolongation of graft survival equal to the negatively tit&red monkey is likely due to the lower weight of this monkey which causes T cells to repopulate faster, in this case 3–4 days faster, due to the larger thymic T cell precursor pool in younger animals. Age related effects such as these can be compensated for by modification of dosage levels and timing of administration.

TABLE II

Efficacy of Anti-CD3 – CRM9 With and Without CRM197 In Rhesus Monkeys With Positive and Negative Anti-Diphtheria Toxin Titers.

| Monkey | Weight kg | Anti-DT Titer | Treatment | Post Treatment* Lymphnode T/B Cell Ratio | Day(s) of Skin Graft Survival |
| --- | --- | --- | --- | --- | --- |
| historical controls | 4–7 | N/A | None | 2.1–2.4$^+$ | 9.5 ± 08$^\$$ |
| B65 | 5.1 | neg | anti-CD3 | 1.8 | 12, 12 |
| 8838 | 5.1 | neg | anti-CD3 – CRM9 | 0.14$^{xx}$ | 19, 20 |
| M93 | 5.1 | 1:1000 | anti-CD3 – CRM9 | 0.57 | 11, 12 |

TABLE II-continued

Efficacy of Anti-CD3 – CRM9 With and Without CRM197 In Rhesus Monkeys With Positive and Negative Anti-Diphtheria Toxin Titers.

| Monkey | Weight kg | Anti-DT Titer | Treatment | Post Treatment* Lymphnode T/B Cell Ratio | Day(s) of Skin Graft Survival |
|---|---|---|---|---|---|
| C81 | 1.0 | 1:1000 | CRM197 + anti-CD3 – CRM9 | 0.20 | 14, 15 |

*All monkeys received the same dose of immunotoxin 0.1 mg/kg total in divided doses on day 0, 1 and 2. Lymph node sampled on day 3. CRM197 when given in 100 fold excess over CRM9 content.
†In this study untreated animals show this lymph node T/B ratio
§Historical controls at TNO, Rijswijk
**Anti-CD3 given at the same mol. dose as anti-CD3 – CRM9

EXAMPLE 8

Immunotoxin UCHT1-CRM9 for the Treatment of Steroid Resistant Graft-Versus-Host Disease Treatment protocols for this type of disease can be expected to last a year, with Patients being followed for at least 5 years.

Characterization of UCHT1-CRM9 and CRM197

UCHT1-CRM9 is a covalent 1:1 conjugate of anti-human CD3 IgG1 monoclonal antibody and CRM9. The conjugate is synthesized, purified, sterile filtered and assayed for concentration, biological efficacy toward target cells and non-target cell toxicity by standardized culture assays. The method of synthesis, purification assay are identical to that used for FN18-CRM9 which was used in the pre-clinical monkey studies described in Examples 5–7.

CRM9 and CRM197 are produced by the Biotechnology Unit, NIH and purified by the Cooperating Facility. UCHT1 is produced in mouse ascites fluid and is purified by affinity chromatography over Protein A Sepharose. The synthesis, purification and storage of UCHT1-CRM9 is performed in a dedicated secure area. UCHT1-CRM9 is purified in 2 mg lots which are pooled and stored at 4° C. Shelf life is documented to be five months at full biological potency but does not exceed 4 months for this study. Preferably, most of the immunotoxin is used within 3 months of synthesis.

Patient Population

The patient population consists of individuals suffering from steroid resistant GVHD whose prognosis is poor. Patients are assayed for anti-CRM9 (anti-DT) titers and antibodies to murine immunoglobulin. Patients having anti-CRM9 titers of 1:1000 and below are treated according to the present protocol. Patients who have a history of receiving murine immunoglobulins or who exhibit positive anti-Ig titers may require special consideration.

Dosage of CRM9 Immunotoxin and Non-Toxic Mutant

UCHT1-CRM9 is administered at a dose which is 1/10 or less of the estimated minimum lethal dose (MLD) in a T lymphopenic patient. The MLD is expected to be at least 0.15 mg/kg (CRM9 content) based on the MLD of 0.15 mg/kg of IgG1-CRM9 in guinea pigs which lack a target cell population for the IgG1. (The presence of target cells in humans raises the MLD by providing a sink for the immunotoxin.) The optimal dose schedule has been found in monkeys to be administration on 3 consecutive days in 3 equally divided doses, and this schedule can be used throughout the treatment period. This permits administration of the total dose before any rise in pre-existing antitoxin titers due to a secondary response. In addition, the initial repopulation from the thymus is also eliminated, thus, further lowering the total T lymphocyte pool. Therefore, a total of 0.0125 mg/kg in three equally divided doses is given to the patient. This dose does induces T cell depletion in monkeys so that monitoring of T cell subsets and signs and symptoms of GVHD is relevant at the lowest dose. For the administration of this dose patients with anti-CRM9 titers of 1:100 or less will be treated. This permits pretreatment doses of CRM197 at 0.33 mg/kg or 1/10 the dose easily tolerated in monkeys. A second dosage group can include patients selected for antitoxin titers of 1:330 or less to whom CRM197 will be given at 1.0 mg/kg. A third dosage group can include patients with 1:1000 antitoxin titers or less will be given CRM197 at 3.3 mg/kg, a dose expected to be tolerable in humans, because it is easily tolerated by monkeys (see Example 7). The monkey MLD data should be very similar to humans on a per weight basis. However, GVHD patients are expected to be more like guinea pigs, because they have a smaller target cell population compared to non-GVHD patients.

Dose escalation can be tested by increasing the dose by a factor of 1.5. The following table exemplifies such a dose escalation test. For example three patients are used in each dosage group. There is a 3 to 4 week delay between each patient so that any late toxicity is detected before a dosage group is completed:

| Patient # | CRM9 Dose each day mg/kg | Total Dose mg/kg | Week ending |
|---|---|---|---|
| 1, 2, 3 | 0.00417 | 0.0125 | 12 |
| 4, 5, 6 | 0.00636 | 0.019 | 24 |
| 7, 8, 9 | 0.0083 | 0.028 | 36 |
| 10, 11, 12 | 0.0125 | 0.042 | 48 |

Assuming each patient weighs on the average 70 kg, the first dosage group will consume 2.6 mg of the CRM9 immunotoxin, and will be supplied as a pool of two 2 mg batches. The second group will consume 3.9 mg and will also be supplied as 2 pooled batches. The third group will require 5.9 mg and will be supplied as three pooled batches. The fourth group will require 8.9 mg and will be supplied as three pooled batches and an additional two pooled batches.

Administration

Prior to administering CRM197 a H1 histamine blocking agent such as Benadryl or Tagevil is given I.V. to minimize any possibility of an anaphylactic reaction (for Benadryl 4 mg/kg). The CRM197 is administered I.V. in a 5 mg/ml sterile filtered solution in phosphate buffered saline pH 7.4 (PBS) over a 5 min time period. The immunotoxin is then given I.V. at 0.2 mg/ml over 2 min time period in a sterile filtered solution of 0.90 mM sodium sulfate and 10 mM sodium phosphate pH 7.4.

Measurements of Biological Parameters

The following parameters can be measured at various intervals during treatment (as exemplified by the schedule below):

A Cytokines, TNF alpha, gamma IFN, IL-6
B Routine clinical chemistries
C WBC, Hct,diff; lymphocyte subsets CD3, CD4, CD8, CD2, CD16, CD20
D Body Weight
E Immune function assays. ELISA assays of serum to monitor antibody responses to UCHT1 (primary response) and CRM9 (secondary response). ELISA assays to monitor antibody responses to polio and DPT reimmunizations done at 1 year following bone marrow transplantation.

| (before IT) | Day 0 | A, B, C, D, E | Also A 2 hrs post |
|---|---|---|---|
| | Day 1 | A, C, D | |
| | Day 2 | A, C, D | |
| | Day 3 | A, B, C, D | |
| | Day 4 | C, D | |
| | Day 7 | A, C, D | |
| | Day 10 | B, C | |
| | Day 14 | A, C, D | |
| | Day 21 | C, D | |
| | Day 28 | A, B, C, D, E | |
| | Day 45 | C, D | |
| | Day 60, | B, C, D, E | |

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of treating an autoimmune disease in an animal comprising administering to the animal a non-toxic mutant of diphtheria toxin followed by an anti-CD3-CRM9 conjugate which routes by the anti-CD3 pathway, or derivatives thereof, under conditions such that the autoimmune disease is treated.

2. The method of claim 1, wherein the non-toxic mutant of diphtheria toxin is CRM197.

3. A method of treating T cell leukemias or lymphomas in an animal comprising administering to the animal a non-toxic mutant of diphtheria toxin followed by an anti-CD3-CRM9 conjugate which routes by the anti-CD3 pathway, or derivatives thereof, under conditions such that the T cell leukemias or lymphomas are treated.

4. The method of claim 3, wherein the non-toxic mutant of diphtheria toxin is CRM197.

5. A method of treating graft-versus-host disease in an animal, comprising administering to the animal a non-toxic mutant of diphtheria toxin followed by an anti-CD3-CRM9 conjugate which routes by the anti-CD3 pathway, or derivatives thereof under conditions such that the graft-versus-host disease is treated.

6. The method of claim 5, wherein the non-toxic mutant of diphtheria toxin is CRM197.

* * * * *